United States Patent
Noteborn et al.

(10) Patent No.: US 7,253,150 B1
(45) Date of Patent: *Aug. 7, 2007

(54) GENE DELIVERY VEHICLE EXPRESSING THE APTOSIS-INDUCING PROTEINS VP2 AND/OR APOPTIN

(75) Inventors: Matheus Hubertus Maria Noteborn, Leiderdorp (NL); Alexandra Maria Pietersen, Leiden (NL)

(73) Assignee: Leadd B.V., Leiden (NL)

( * ) Notice: Subject to any disclaimer, the term of this patent is extended or adjusted under 35 U.S.C. 154(b) by 0 days.

This patent is subject to a terminal disclaimer.

(21) Appl. No.: 09/403,213

(22) PCT Filed: Apr. 15, 1998

(86) PCT No.: PCT/NL98/00213

§ 371 (c)(1), (2), (4) Date: Jun. 22, 2000

(87) PCT Pub. No.: WO98/46760

PCT Pub. Date: Oct. 22, 1998

Related U.S. Application Data

(63) Continuation-in-part of application No. 08/482,161, filed on Jun. 7, 1995, now Pat. No. 6,162,461, which is a continuation-in-part of application No. 08/454,121, filed as application No. PCT/NL94/00168 on Jul. 19, 1994, now Pat. No. 6,071,520, which is a continuation-in-part of application No. 08/030,335, filed as application No. PCT/NL91/00165 on Sep. 11, 1991, now Pat. No. 5,491,073.

(30) Foreign Application Priority Data

Apr. 15, 1997 (EP) ................................. 97201121
Nov. 18, 1997 (EP) ................................. 97203595

(51) Int. Cl.
*A01N 43/04* (2006.01)
*A61K 31/70* (2006.01)

(52) U.S. Cl. ............... 514/44; 424/93.2; 435/320.1; 435/353; 435/354; 435/369; 435/368; 435/370; 435/455; 435/456; 435/325

(58) Field of Classification Search ............ 514/44; 424/9.2, 93.2; 425/455; 435/320.1, 325, 435/455, 456, 353, 366, 369, 368, 354, 370
See application file for complete search history.

(56) References Cited

U.S. PATENT DOCUMENTS

| | | | | |
|---|---|---|---|---|
| 5,643,770 A | * | 7/1997 | Mason et al. | 435/172.3 |
| 5,656,465 A | * | 8/1997 | Panicali et al. | 435/456 |
| 5,661,126 A | * | 8/1997 | Donahoe et al. | 514/12 |
| 5,922,600 A | * | 7/1999 | Noteborn et al. | 435/456 |
| 5,952,002 A | * | 9/1999 | Noteborm et al. | 424/450 |
| 5,981,502 A | * | 11/1999 | Noteborn et al. | 514/44 |
| 5,994,128 A | * | 11/1999 | Fallaux et al. | 435/325 |
| 6,071,520 A | * | 6/2000 | Noteborn et al. | 424/186.1 |
| 6,162,461 A | * | 12/2000 | Noteborn et al. | 424/450 |
| 6,197,293 B1 | * | 3/2001 | Henderson et al. | 424/93.2 |
| 6,217,870 B1 | * | 4/2001 | Noteborn et al. | 424/184.1 |
| 6,251,433 B1 | * | 6/2001 | Zuckermann et al. | 424/486 |
| 6,472,142 B1 | * | 10/2002 | Noteborn et al. | 435/4 |
| 6,620,925 B1 | * | 9/2003 | Noteborn | 536/23.5 |

FOREIGN PATENT DOCUMENTS

WO  WO 95/03414  * 2/1995
WO  WO 96/30512  * 10/1996

OTHER PUBLICATIONS

Fallaux et al., Characterization of 911: a new helper cell line for the titration and propagation of early region 1-deleted adenoviral vectors, 1996, Human Gene Therapy, vol. 7, pp. 215-222.*
Pietersen et al., Specific tumor-cell killing with adenovirus vectors containing the apoptin gene, 1996, Gene Therapy, vol. 6, pp. 882-892.*
Verma et al., Gene therapy-promises, problems and prospects, 1997, Nature, vol. 389, pp. 239-242.*
Anderson, Human gene therapy, 1998, Nature, vol. 392, pp. 25-30.*
Vile et al., Cancer gene therapy: hard lessons and new courses, 2000, Gene Therapy, vol. 7, pp. 2-8.*
Chiu et al., Optimizing energy potentials for success in protein tertiary structure prediction, 1998, Folding & Design, vol. 3, pp. 223-228.*
JT Ngo et al., The Protein Folding Problem and Tertiary Structure Prediction, "Computational Complexity, Protein Structure Prediction, and the Levinthal Paradox," 1994,pp. 433 and 492-495.*
Yuasa et al. Avian Disease, vol. 23, 1979, pp. 366-385.*
Chao et al., Biochem J., vol. 286, part 2, pp. 555-559, 1992.*
Levrero et al., Defective and nondefective adenovirus vectors for expressin foreign gene in vitro and in vivo, Gene, 1991, pp. 195-202, vol. 101.
Noteborn et al, A single Anaemia Virus Protein, Apoptin Causes Cytopathogenic Effect by Inducing Apoptosis, pp. 376-381.

(Continued)

Primary Examiner—Joseph Woitach
Assistant Examiner—Brian Whiteman
(74) Attorney, Agent, or Firm—TraskBritt

(57) ABSTRACT

The invention relates to gene delivery vehicles which comprise nucleic acid molecules encoding apoptosis-inducing proteins VP2 and/or apoptin (VP3) like activity. VP2 and VP3 are viral proteins of the Chicken Anaemia Virus. Also, the invention relates to anti-tumor therapies. Infection of various human tumor cells with the gene delivery vehicles of the invention will result in the induction of apoptosis in tumor cells and much reduced apoptosis, if at all, in normal diploid, non-transformed/non-malignant cells. Also the invention relates to the diagnosis of cancer, and related forms of hyperplasia, metaplasia and dysplasia.

17 Claims, 7 Drawing Sheets

OTHER PUBLICATIONS

Noteborn et al., A Single Chicken Anemia Virus Protein Induces Apoptosis, Journal of Virology, Jan. 1994, pp. 346-351, vol. 68, No. 1.

Noteborn et al., Chicken anaemia virus infection: molecular basis of pathogenicity, Avian Pathology, 1995, pp. 11-31, vol. 24.

Noteborn et al., Characterization of Cloned Chicken Anemia Virus DNA That Contains All Elements for the Infectious Replication Cycle, Journal of Virology, Jun. 1991, pp. 3131-3139, vol. 65, No. 6.

Zhuang et al., Apoptin, a Protein Derived from Chicken Anemia Virus, Induces p53-independent Apoptosis in Human Osteosarcoma Cells, Cancer Research, Feb. 1, 1995, pp. 486-489, vol. 55.

Zhuang et al., Apoptin, a Protein Encoded by Chicken Anemia Virus, Induces Cell Death in Various Human Hematologic Malignant Cells in vitro, Leukemia, 1995, pp. S118-S120, vol. 9, Suppl. 1.

* cited by examiner pMad5 9270 bp

Ad5-5'PvuII (ITR, packaging signal)
Major late promotor (MLP)
Tripartite leader (tpl)
Ad5-BglII fragment (nt 3328-8914 Ad5)
b lactamase

BamH1-ClaI Linker
5'-GATCCCGCACGCGTGCGAT-3' SEQ ID NO:5
3'- GGCGTGCGCACGCTAGC-5' SEQ ID NO:6 pMab 9306 bp pMabvp3 9756 bp pMabcon 9756 bp pMabvp2 10456 bp pMabcon2 10456 bp retroviral VP3 vector:

GENE DELIVERY VEHICLE EXPRESSING THE APTOSIS-INDUCING PROTEINS VP2 AND/OR APOPTIN

This application is a continuation-in-part of U.S. application Ser. No. 08/482,161, filed Jun. 7, 1995, now U.S. Pat. No. 6,162,461, issued Dec. 19, 2000, which is a continuation-in-part of application Ser. No. 08/454,121, filed Nov. 30, 1995, which is a national stage application under 35 U.S.C. § 371 of international application No. PCT/NL94/00168, filed Jul. 19, 1994, now U.S. Pat. No. 6,071,520, issued Jun. 6, 2000, which is a continuation-in-part of Ser. No. 08/030,335, filed Mar. 8, 1993, now U.S. Pat. No. 5,491,073, issued Feb. 13, 1996, filed as a national stage application under 35 U.S.C. § 371 of international application No. PCT/NL91/00165, filed Sep. 11, 1991.

The invention relates to gene delivery vehicles which comprise nucleic acid molecules encoding apoptosis-inducing proteins VP2 and/or apoptin (VP3) like activity.

Also, the invention relates to anti-tumor therapies and to the diagnosis of cancer. Infection of various human tumor cells with the gene delivery vehicles of the invention will result in the induction of apoptosis in tumor cells and much reduced apoptosis, if at all, in normal diploid, non-transformed/non-malignant cells.

In vitro, expression of the chicken anemia virus (CAV)-derived protein apoptin (VP3) in chicken transformed cells induced apoptosis (Noteborn et al. 1994, Noteborn and Koch, 1995). Apoptosis is characterized by shrinkage of cells, segmentation of the nucleus, condensation and cleavage of DNA into domain-sized fragments, in most cells followed by internucleosomal degradation. Finally, the apoptotic cells fragment into membrane-enclosed apoptotid bodies, which are rapidly phagocytosed by neighbouring cells. Therefore, apoptosis causes much less destruction of tissue than necrosis, the non-physiological type of cell death (Wyllie et al., 1980, Arends and Wyllie, 1991 and White, 1996).

Apoptin is a small protein, only 121 amino acids long, which is rather basic, and proline-, serine- and threonine-rich (Noteborn et al. 1991). In the analysed transformed chicken cells, and which all undergo apoptin-induced apoptosis, apoptin is located strictly within the cell nucleus. Truncation of the C-terminal basic stretch of apoptin results in a reduced nuclear location and a significantly reduced apoptotic activity (Noteborn et al., 1994).

Apoptin, and other proteins with apoptin-like activity, can also induce apoptosis in human malignant and transformed cell lines, but not in untransformed human cell lines. We have established that apoptin-induced apoptosis occurs in the absence of functional p53 (Zhuang et al., 1995a), and cannot be blocked by Bcl-2, BCR-ABL (Zhuang et al., 1995), the Bcl-2-associating protein BAG-1 and the cowpox protein CrmA (Noteborn, 1996). In vitro, apoptin fails to induce programmed cell death in normal lymphoid, dermal, epidermal, endothelial and smooth-muscle cells. However, when normal cells are transformed they become susceptible to apoptosis by apoptin or other proteins with apoptin-like activity. Long-term expression of apoptin in normal human fibroblasts revealed that apoptin has no toxic or transforming activity in these cells. In normal cells, apoptin was found predominantly in the cytoplasm, whereas in transformed or malignant cells i.e. characterised by hyperplasia, metaplasia or dysplasia, it was located in the nucleus, suggesting that the localization of apoptin is related to its activity (Danen-Van Oorschot et al., 1997, Noteborn, 1996).

Apoptosis is an active and programmed physiological process for eliminating superfluous, altered or malignant cells (Earnshaw, 1995). The apoptotic process can be initiated by a variety of regulatory stimuli (Wyllie, 1995 and White, 1996). Changes in the cell survival rate play an important role in human pathogenesis, e.g. in cancer development, which is caused by enhanced cell proliferation but also by decreased cell death (Kerr et al., 1994). A variety of chemotherapeutic compounds and radiation have been demonstrated to induce apoptosis in tumor cells, in many instances via wild-type p53 (Thompson, 1995, Bellamy et al., 1995, Steller, 1995).

Many tumors, however, acquire a mutation in p53 during their development, often correlating with poor response to cancer therapy (Hooper, 1994). For several (leukemic) tumors, a high expression level of the proto-oncogene Bcl-2 is associated with a strong resistance to various apoptosis-inducing chemotherapeutic agents (Hockenberry, 1994, Kerr et al., 1994, and Sachs and Lotem, 1993).

Therefore, apoptin may become a potential candidate for the destruction of tumor cells, or other cells characterised by hyperplasia, metaplasia or dysplasia, which have become resistant to (chemo)therapeutic induction of apoptosis, due to the lack of functional p53 and (over)-expression of Bcl-2 and other apoptosis-inhiting agents. The fact that apoptin does not induce apoptosis in normal non-transformed human cells, at least not in vitro, suggests that a toxic effect of apoptin treatment in vivo might be very low.

However, thus far, expression of apoptin in tumor cells is carried out by using transient transfection of tissue-culture cells. The disadvantage of this expresssion method is the very low percentage of cells, which can express apoptin under in vitro circumstances. In vivo, the used transfection methods will be cumbersome and not efficient, if possible at all, and will not at all contribute to effective cancer treatment.

Adenovirus can be derived from human adenoviruses (Ads), which are non-enveloped, icosahedral DNA viruses. The genome consists of a linear, double-stranded DNA molecule of about 36 kb carrying inverted terminal repetitions (Horvitz, 1990). The serotypes that have been used for vector development (Ad2 and Ad5) are not associated with severe human pathology (Horvitz, 1990). The virus is extremely efficient in introducing its DNA into the host cell. Ads can infect a wide variety of dividing and non-dividing cells of a broad range of species, and the virus can be produced in large quantities with relative ease. In contrast to retroviruses, Ads do not integrate into the host cell genome. All currently used rAdVs have a deletion in the E1 region, where novel DNA can be introduced. The E1 deletion renders the recombinant virus replication-defective (Stratford-Perricaudet and Perricaudet, 1991). On the one hand, this provides an essential safety feature: the rAdV cannot replicate on human cells in the absence of E1A proteins. Thus, the rAdV can deliver its genetic information in a human cell, but this will not result in a lytic or productive infection. On the other hand, it poses a problem for the production of these vectors. However, the E1 functions need not necessarily to be encoded by the vector itself. They can also be provided in trans, in special helper cells, which express the E1 genes. Upon infection or transfection of these helper cells with an E1-deleted Ad vector, the cellular E1 proteins will complement the replication of the rAdV, which results in the production of progeny rAdVs. Ad helper cells must be of human origin, and they must contain and express the AdE1 region, i.e. Ad-transformed human cells such as cell line 293 (Graham and Prevec, 1991), the 911 cell line (Fallaux et al., 1996) and the PER.C6 cell line (Fallaux, 1996).

The invention now provides a gene delivery vehicle (or vector) which enables using the features of the anti-tumor agent apoptin, or other proteins with apoptin-like activity, for cancer treatment via the use of gene-therapy, or for the treatment of malignancies characterized by hyperplasia, metaplasia or dysplasia. Such a gene delivery vehicle, which is a independently infectious vector can for example be a virus, or a liposome, or a polymer, or the like, that in it self can infect or in any other way deliver genetic information to for example tumor-cells that can be treated. The genetic information comprises a nucleic acid molecule encoding apoptin-like activity. The invention also provides a gene delivery vehicle that greatly has been increased in its capacity to express apoptin-like activity. Surprisingly, it was found that changing upstream non-coding nucleic acid sequences, located within the translation initiation site, that precede apoptin-like protein coding sequences greatly enhances expression of said protein in tumor cells. The invention also provides a gene delivery vehicle comprising a nucleic acid encoding a VP2-like activity. VP2-like activity, surprisingly, was shown to act synergistically with apoptin-like activity concerning the induction of apoptosis in tumor cells, VP2-like protein in it self can also act synergistically or additive to for example (chemo)therapeutic induction of apoptosis. The invention also provides a gene delivery vehicle comprising a nucleic acid encoding a VP2-like activity additionally to comprising a nucleic acid molecule encoding apoptin-like activity. Provided by the invention is for example a gene delivery vehicle acording to the invention that is a virus. Additionally, the invention provides a gene delivery vehicle that in it self is replication-defective virus but which can replicate in helper or packaging cells to generate progeny gene delivery vehicles. The gene delivery vehicle thus provided by the invention can for instance be an adenovirus, or an retrovirus or other DNA or RNA recombinant viruses that can be used as delivery vehicle or a plasmovirus. Additionally, the invention provides a gene delivery vehicle which has additionally been supplemented with a specific ligand or target molecule or target molecules, by which the gene delivery vehicle can be specifically directed to deliver its genetic information at a target cell of choice. Such a target molecule can for instance be a viral spike protein, or receptor molecule, or antibody, reactive with a tumor cell surface receptor or protein.

Also, the invention provides a gene delivery vehicle which can be used in the diagnosis i.e. of cancer. Such a gene delivery vehicle can i.e. be used for in vitro diagnosis, wherein tissue or cell samples or biopsies are taken from a human or animal. Such samples can then be evaluated or tested by infecting them, in culture or directly, with said gene delivery vehicle capable of expressing i.e. apoptin-like activity. Only transformed cells, or cells displaying various stages of hyperplasia, dysplasia or metaplasia, or tumor or cancer cells, express protein with apoptin-like activity within the nucleus. The presence of said protein can i.e. be demonstrated with classical (immuno) histochemical techniques i.e. microscopically or with automated cell sorting techniques. Alternatively, the above infected cells are characterized by apoptosis and can thus be diagnosed on the known characteristics of apoptosis.

The invention furthermore provides or describes all steps needed for the construction of a recombinant, replication-defective adenovirus expressing the apoptosis-inducing agent apoptin. High titres of recombinant-apoptin adenovirus can be produced by, means of adenovirus packaging cell lines, such as 293, 911' and PER.C6. Apoptin does not exhibit a detectable negative effect on all necessary adenovirus replication steps and other adenovirus life-cycle events under cell culture conditions.

In addition, the invention describes the construction of a control recombinant adenovirus, which contains all sequences as the recombinant-apoptin adenovirus, but due to the 3'–5' orientation of the apoptin-encoding sequence under control of the regulating promoter elements, not able to express apoptin. By means of this control adenovirus vector, the specific effects of apoptin expression by a recombinant adenovirus can be examined.

Recombinant replicative-defective adenovirus expresses apoptin in high amounts in various tumor and/or transformed cells resulting in the induction of apoptosis. In contrast, expression of apoptin in normal non-transformed human cells by means of recombinant adenoviruses does not result in the induction of apoptin-induced apoptosis.

In particular, the invention relates to anti-tumor therapies. Treatment of tumor (cell)s will take place by expression of apoptin by means of infecting (tumor) cells with gene delivery vehicles such as adenovirus vectors that contain a coding sequence for a protein with apoptin-like activity. Therefore, the invention provides gene delivery vehicles such as the adenovirus expressing apoptin which is a very potential anti-tumor agent. Adenovirus regulation of apoptin does not or at least not detectable induce apoptosis in normal cells, indicating that the toxicity of in-vivo treatment with recombinant-apoptin adenovirus will be low. By means of recombinant-apoptin adenovirus infection a much higher amount of apoptin-expressing (tumor) cells can be achieved. This finding is an major improvement of apoptin expression in comparison to DNA transfections.

The invention relates also to the construction of a VP2 expression unit without the synthesis of apoptin and/or a part of apoptin. Furthermore, we have provided evidence that expression of the chicken anemia virus (CAV) protein VP2 enhances the apoptin-induced apoptosis in human tumor cells. To be more precise VP2 and apoptin acts synergistically concerning induction of apoptosis in tumor cells. This finding indicates that co-expression of VP2 and apoptin will result in an improvement of apoptin-based therapies.

The invention describes the significant improvement of apoptin expression by changing its direct upstream sequences of the ATG-initiation codon. The improvement of expression does not need a amino acid change in the apoptin protein, as was predicted by the KOZAK rule. Improvement of upstream sequences of the ATG-initiation codon of the other CAV proteins will also result in improvement of their synthesis.

The invention also relates to the construction of retroviral vectors, which express apoptin in human tumor cells resulting in the induction of apoptosis. This result with recombinant-apoptin retrovirus in combination with the recombinant-apoptin adenovirus data indicate that apoptin expression is not toxic for the replication of a DNA- and RNA-virus.

Expression of apoptin in (tumor) cells may also take place by infecting cells with other DNA and/or RNA-viral vectors, besides adenovirus or retrovirus vectors, that contain a coding sequence for apoptin. In addition, virus-derived vector systems, such as plasmoviruses can be used for the induction of apoptin-induced apoptosis in tumor cells.

The invention will be explained in more detail on the basis of the following experimental part. This is only for the purpose of illustration and should not be interpreted as a limitation of the scope of protection.

DETAILED DESCRIPTION OF THE INVENTION

Figure 1:
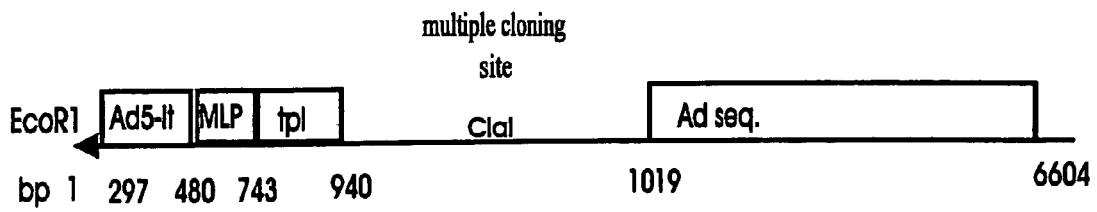
FIG. 1 shows the diagrammatic representation of the essential parts of the adenovirus adaptor vectors pMAd5 and pMab.
Figure 1:
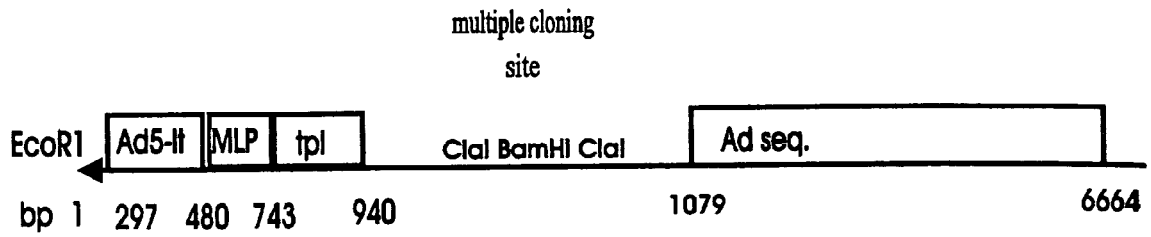

Cells and cell culture conditions.

Ad5 E1-transformed human embryonic kidney (HEK; 293) and human embryonic retina (HER; 911 and PER.C6) cell lines were grown in Dulbecco's modified Eagle medium (DMEM) supplemented with 10% fetal calf serum (FCS) in a 5% CO2 atmosphere at 37° C. Cell line 293 was obtained from the American Type Culture Collection (ATCC CRL 1573). Cell lines 911 and PER.C6 were obtained from Fallaux et al. (1996). Cell culture media, reagents, and sera were purchased from GIBCO Laboratories (Grand Island, N.Y.) Culture plastics were purchased from Greiner (Nürtingen, Germany).

Human epidermal keratinocytes were isolated from foreskin and grown in the presence of a layer of mouse 3T3 fibroblasts lethally irradiated with 137-Cs. Primary cultures of keratinocytes (FSK-1) were initiated in complete medium as described (Rheinwald and Green, 1975) with minor modifications.

Tumorigenic keratinocytes, SCC-15 cells (Rheinwald and Beckett, 1981), derived from squamous-cell carcinoma, were cultured in DMEM/F12 (3:1) medium containing 5% fetal calf serum, 0.4 ug hydrocortisone and 1 uM isoproterenol. The human hepatoma-derived HepG2 cells (Aden et al., 1979) and the human osteosarcoma-derived U2OS and Saos-2 cells (Diller et al., 1990) were grown in DMEM (GIBCO/BRL) supplemented with 10% fetal calf serum. The spontaneously transformed keratinocyte strain HaCaT (Boukamp et al., 1988) was a gift from Prof. Dr. R. Fusenig, DKFZ, Heidelberg, Germany. HaCAT cells were grown in DMEM supplemented with 10% fetal calf serum.

Murine cell lines were cultivated in Dulbecco's modified Eagle medium with high glucose (4.5 gram per liter) and 10% fetal calf serum in a 5% CO2 atmosphere at 37° C. The ecotropic packaging cell line Psi-2 (Mann et al., 1983) and the amphotropic packaging cell line PA317 have been described before (Miller, 1990a,b).

Virus techniques.

Plaque assays were performed as described previously (Fallaux et al., 1996). Briefly, adenovirus stocks were serially diluted in 2 ml DMEM containing 2% horse serum and added to near-confluent 911 cells in 6-well plates. After 2 h incubation at 37° C., the medium was replaced by F-15 minimum essential medium (MEM) containing 0.85% agarose (Sigma, USA), 20 mM HEPES (pH 7.4), 12.3 mM MgCl2; 0.0025% L-glutamine, and 2% horse serum (heat-inactivated at 560 C for 30 minutes).

Small-scale production of adenovirus lots was performed as described previously (Fallaux et al., 1996). Briefly, near-confluent 911 ot PER.C6 monolayers were infected with approximately 5 plaque-forming units (p.f.u._s) per cell, in phosphate-buffered saline (PBS) containing 1% horse serum. After 1 hour at room temperature, the inoculum was replaced by fresh medium (DMEM/2% horse serum). After 48 hours, the nearly completely detached cells were harvested, and collected in 1 ml PBS/1% horse serum. Virus was isolated from the producer cells by 3 cycles of flash-freeze/thawing. The lysates were cleared by centrifugation at 3000 rpm fr 10 minutes, and stored at −20° C.

The 911 and PER.C6 produced rAdV stocks were screened for the presence of recombinant-competent adenovirus by5 performing PCR analysis with primers derived from the Ad5 ITR region (5'-GGGTGGAGTTTGT-GACGTG-3') SEQ ID NO:1 and the E1A encoding region (5'-TCGTGAAGGGTAGGTGGTTC-3') SEQ ID NO:2 as described by Noteborn and De Boer (1995) using a Perkin Elmer PCRapparatus. The presence of a 600-bp amplified fragment indicates that replication-competent (E1-region containing) adenovirus exists in the analyzed virus stock (Hoeben, unpublished results) or by infecting HepG2 cells with rAdV batch. During a period of at least 10 days, the cells were monitored for potential cytopathogenic effects and by indirect immunofluorescence using a specific monoclonal antiserum directed against E1A protein.

Plasmids and DNA transfections.

The adaptor plasmid pMad5 was constructed from pMLP10 (Levrerno et al. 1991) as described below, Plasmid, pMLP-10-lin was derived from pMLP10 by insertion of a synthetic DNA fragment with unique sites for the restriction endonucleases MluI, SplI, SnaBI, SpI AsuII, and MunI into the HindIII site of pMLP10. The adenovirus BglII fragment spanning nt 3328 to 8914 of the Ad5 genome was inserted into the MunI site of pMLP-lin. From the resulting plasmid, the SalI-BamHI fragment was deleted to inactivate the tetracycline resistance gene. The resulting plasmid was controlled by restriction-enxyme analysis and named pMad5. Expression of genes inserted in the multiple cloning site will be driven by the adenovirus major late promoter, which in this configuration is linked to the adenovirus immediate-early gene 1 (E1) enhancer.

All CAV DNA sequences are originally derived from the plasmid pIc-20H/CAV-EcoRI (Noteborn and De Boer, 1990). The expression plasmid pCMV-fs, formerly called pCMV-VP3 (Noteborn et al. 1994), contains CAV DNA sequences encoding apoptin exclusively (nt 427–868).

The plasmid pCMV-VP2mu (Noteborn, unpublished results) contains CAV DNA sequences of positions 380 to 1512. This CAV DNA fragment contains the coding region for VP2 flanked by 25 bp 5'-non-coding and 484 bp 3'-non-coding CAV DNA sequences. 106 bp downstream of the start codon for VP2 the start codon for apoptin is situated in another reading frame. To prevent the synthesis of apoptin without interfering the VP2 synthesis a mutation in the apoptin-initiation codon (ATG was changed into ACG) was introduced and in addition a point-mutation at position 549 (T was changed into an A), resulting in an extra stopcodon within the gene encoding apoptin. Therefore, the inserted CAV sequences will only express full-length VP2 protein. By indirect immunofluorescence was shown that VP2 can be produced but that apoptin was not synthesized.

For the cloning of PCR-amplified DNA fragments, we have used plasmid pCR-3.1, which was purchased commercially from InVitrogen (Carlsbad, Calif.). For the construction of a recombinant-apoptin replication-defective retrovirus, the retrovirusvector pLXSN was used (Miller, 1990a,b).

All cloning steps with plasmid DNAs were in principle carried out according the methods by Maniatis et al. (1992).

All used enzymes were commercially obtained from Boehringer Mannheim, Germany and/or BioLabs, USA.

Plasmid DNA was purified by centrifugation in a CsCl gradient and column chromatography in Sephacryl S500 (Pharmacia, Uppsala, Sweden). The human cell lines HaCAT, HepG2, SCC-15, 293, 911, and PER.C6 were transfected with plasmid DNA by calcium-phosphate precipitation as described by Graham and Van der Eb (1973). Normal human diploid keratinocytes (FSK-1; second passage), U2OS and Saos-2 cells were transfected with DOTAP (Fischer et al., 1996).

Indirect immunofluorescence assay.

Cells were fixed with 80% acetone and used for immunofluorescence assays with CAV-specific or adenovirus E1A-specific monoclonal antibodies and goat anti-mouse and/or goat anti-rabbit IgC conjugated with fluorescein (Jackson Immunoresearch Laboratories Inc., West Grove Pa.), as described by Noteborn et al. (1990). Nuclear DNA was stained with 2,4-diamino-2-phenylindole (DAPI) or propidium iodide (PI).

Results and Discussion

Construction of the Adaptor Vector pMab

To introduce a BamHI restriction-enzyme site into the adaptor plasmid pMAd5, it was digested with the restriction enzyme ClaI and treated with calf intestine alkaline phosphatase. A ClaI-BamHI linker was treated with T4-kinase and ligated to itself by using T4-DNA ligase and subsequently by ClaI digestion. The ClaI/BamHI/ClaI linker was isolated and ligated to the linearized pMad5 vector. The bacterial strain JM109 was transformed with the ligation products.

By restriction-enzyme digestions, the final vector pMab was characterized. By means of the pMab vector foreign genes can be ligated into the unique BamH1 site under regulation of the adenovirus major late promoter. A schematic representation of pMad5 and pMab is shown in FIG. 1.

Construction of a Recombinant-apoptin and Control Adaptor Vector

To construct a adaptor vector for introducing the apoptin gene into a adenovirus, pMab was treated with BamHI and subsequently with calf intestine phosphatase. Subsequently, pCMV-fs was treated with BamH1 and a 0.45 kb DNA fragment containing the apoptin-encoding sequences was isolated. The apoptin DNA fragment was ligated into the BamHI site of the linearized pMab adaptor vector. The ligation products were cloned into the baterial strain JM109. The orientation of apoptin in pMab was determined by restriction-enzyme analysis.

Figure 2:
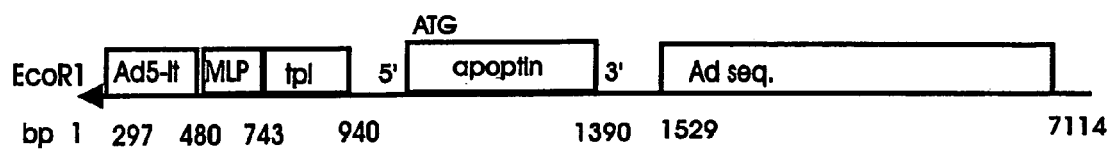
FIG. 2 shows the diagrammatic representation of the essential parts of the recombinant adenovirus adaptor vectors pMab-VP3 and pMab-con.
Figure 2:
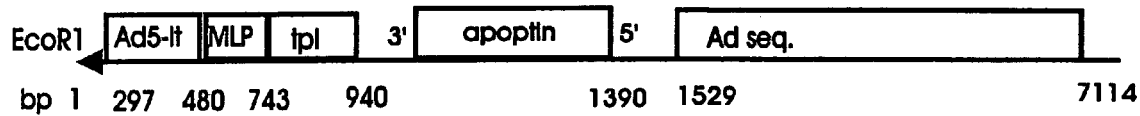

The pMab construct containing the apoptin gene in the 5'–3' orientation under the regulation of the adenovirus major late promoter will express the apoptin gene. This adaptor vector is called pMab-VP3 and will be used to generate a adenovirus vector expressing apoptin. The pMab DNA plasmid containing the apoptin-encoding sequences in the 3'–5' orientation downstream of the adenovirus major late promoter cannot express apoptin and will be used to make a control recombinant adenovirus vector. A schematic representation of both recombinant adaptor vectors is shown in FIG. 2.

Induction of apoptosis by a CMV-plasmid versus a recombinant-apoptin adaptor vector expressing apoptin.

Firstly, we have examined whether the pMab-VP3 DNA vector is indeed able to express apoptin in transfected cells, whereas pMab-con should not do so. To that end, human adenovirus-transformed 293 and 911 cells were transfected with pMab-VP3, pMab-con, and as positive control with pCMV-VP3. Approximately two days after transfection, the cells were fixed and examined for expression of apoptin by means of an indirect-immunofluorescence assay. The cell cultures transfected with pCMV-VP3 and pMab-VP3 contained about 1% of the cells reacting with an apoptin-specific monoclonal antibody, whereas cell-cultures transfected with pMab-con DNA did not. These results imply that pMab-VP3 expresses apoptin and as expected pMab-con not.

In an other transfection experiment, we have analysed the induction of apoptosis in 911 cells after transfection with pMab-VP3 versus pCMV-VP3. Three days after transfection, the 911 cells were harvested and examined by indirect-immunofluorescence for expression of apoptin. In addition, the cells were stained with DAPI or PI, which stain intact DNA strongly, but apoptotic DNA weakly and/or irregularly (Telford, 1992).

Figure 3:
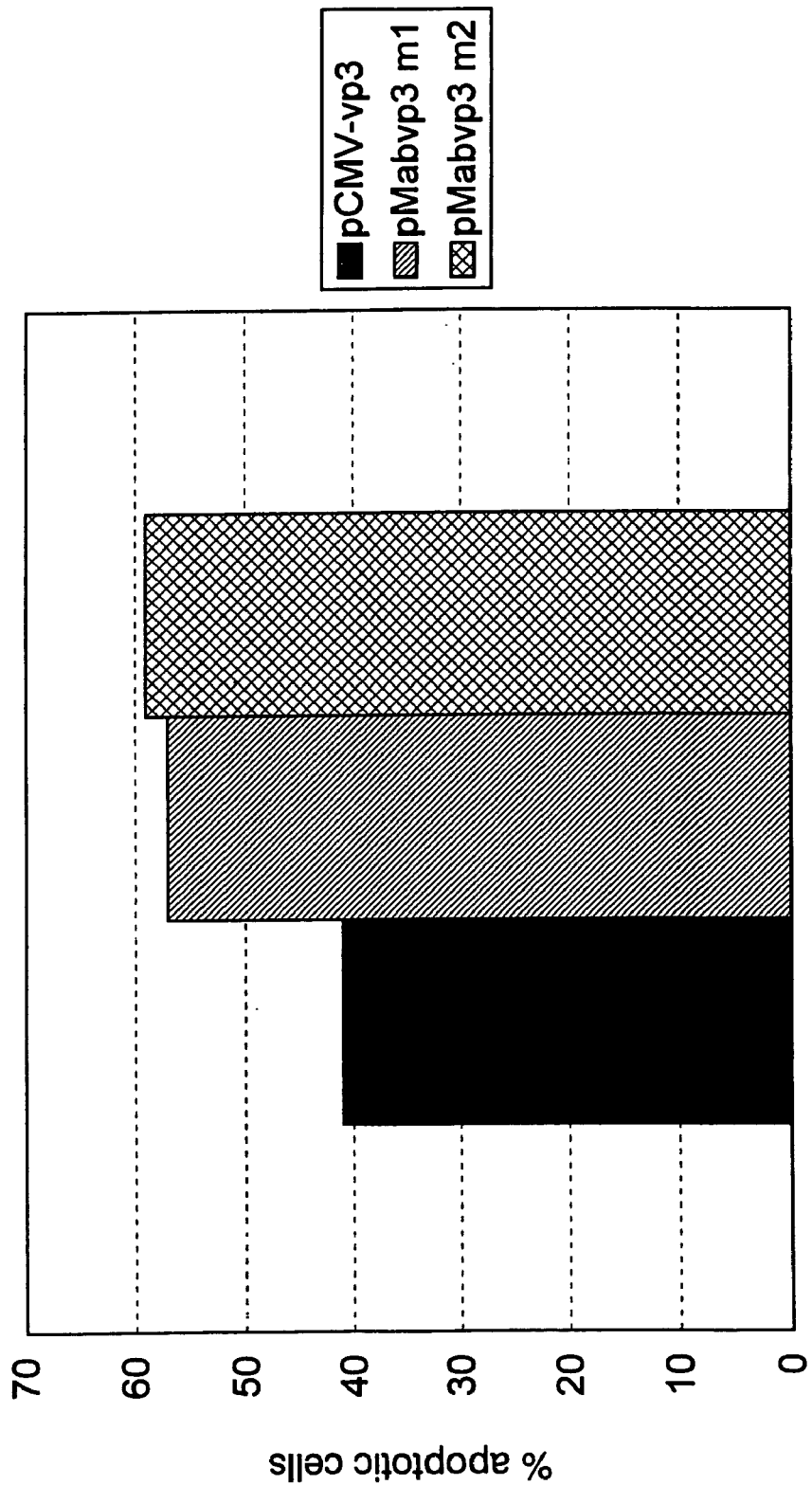
FIG. 3 shows the apoptin-induced apoptosis activity in 911 cells transfected with pMAb-VP3 or pCMV-VP3. Two independently cloned and purifies pMab-VP3 DNA-batches (pMab-VP3/ml and pMab-VP3-m$^2$) were used for the transfection of 911 cells. The cells were fixed 3 days after transfection and analyzed by indirect immunofluorescence using the apoptin-specific monoclonal antibody CVI-CAV-85.1 (85.1; Noteborn et al., 1981). The percentage of cells that stained abnormally with DAPI is given as a relative measure for apoptosis.

Approximately 60% of the apoptin-positive 911 cells, transfected with pMab-VP3 were apoptotic, whereas around 40% of the apoptin-postive cells, transfected with pCMV-VP3 underwent apoptosis. These results indicate that pMab-VP3-regulated expression of apoptin results in a similar or somewhat higher level of apoptosis induction, than apoptin expressed by pCMV-VP3. The results are shown in FIG. 3.

Furthermore, apoptin is able to induce apoptosis in human adenovirus-transformed cells, E1B does not inhibit apoptosis induced by apoptin. In contrast, E1B is able to block apoptosis induced by a great variety of chemotherapeutic agents. These results indicate that apoptin is a very potent anti-tumor agent.

Construction of Recombinant-apoptin Adenovirus

Recombinant-apoptin adenovirus vectors were generated by co-transfection into helper cell line 911 of adaptor plasmids pMab-VP3 carrying the coding sequences for apoptin plus some adenovirus sequences, and plasmid DNA JM17 containing the entire adenovirus DNA minus the E1 and E3 region (McGrory et al., 1988). The co-transfections were transformed with calcium-phosphate-precipitated DNA as described by Graham and Van der Eb (1973). The recombinant adenovirus DNA is formed by homologous recombination between the homologous viral sequences that are present in the plasmid pMAb-VP3 and the adenovirus DNA of JM17 DNA.

In a similar way, co-transfections of 911 cells were carried out with pMab-con and pJM17 DNA to generate the control recombinant adenovirus that cannot express apoptin, and which will be used as adenovirus control for the apoptin-induced apoptotic effects.

Several hours after transfection, the 911 cell monolayers were covered with an agarose overlayer and incubated at 37° C. until recombinant adenovirus-induced plaques became clearly visible. The virus was harvested from plaques as PBS-horse serum stocks, as described by Fallaux et al. (1996). Subsequently, a part of the recombinant-virus stocks was added to 24-wells containing fresh 911 cells. Several days later, these infected 911 cells were lysed and the recombinant viruses were harvested.

Next, the expression of apoptin by the potential recombinant-apoptin adenoviruses (rAd-VP3) or its absence of expression by control recombinant adenoviruses' (rAd-con) was examined. A part of the recombinant virus stocks derived from the infected 24-wells plates were used to infect fresh 911 cells, which were grown as monolayers on glass cover slips. One day later, the infected 911 cells were fixed with aceton and analysed by immunofluorescence using the apoptin-specific monoclonal antibody 85.1. Five out of 5 analysed 911 cell cultures infected with putative rAd-VP3, contained cells expressing apoptin. None of the 911 cells infected with Ad-con and non-infected 911 cells were positive for apoptin.

These results imply that upon co-transfection of adenovirus packaging cell lines, such as 911 cells, with the required adaptor and adenovirus DNA, viable rAd-VP3 expressing apoptin can be generated.

Two stocks derived from rAd-VP3 or rAd-con plaques were used for purifying the rAds by carrying out three subsequent plaque purifications with 911 cells or in parallel a limited-dilution assay on PER.C6 cells as described by Fallaux (1996).

Based on the above described methods resulting in the production of rAd-VP3 expressing apoptin under the regulation of the adenovirus major late promoter, we also succeeded in an adenovirus vector expressing apoptin under the control of a cytomegalovirus (CMV) promoter. These results show that various types of recombinant adenoviruses can be produced regulating by one of its own or heterologous promoter elements.

Production of rAd-VP3 and rAd-con by Using PER.C6 Cells

Small-scale production of rAd-VP3 and rAd-con lots using PER.C6 cells were performed as described (Fallaux, 1996). Briefly, the procedure is described in the Experimental section.

By plaque-assay, the titres were determined to be approximately $10^{11-12}$ per ml cleared lysate for both rAd-VP3 and rAd-con. The obtained titres are not lower than observed in our laboratory for other rAd's.

By means of the PCR-analysis and infection of HepG2 with rAd-VP3 and rAd-con was examined whether the produced virus batches contained replication competent adenovirus (see also Experimental section). Both the rAd-VP3 and rAd-con batches were free of RCA, as proven by both methods.

We conclude that the expression of apoptin does not negatively interfere with all required steps of the adenovirus life cycle under cell-culture conditions. Therefore, a gene-therapy based on an adenovirus vector expressing apoptin is feasible.

Due to the expression of the anti-apoptotic Ad5 E1 proteins (White, 1996), apoptin optimally induces apoptosis after the recombinant-apoptin adenovirus has been produced in high amounts. The fact, that an adenovirus vector expressing apoptin can be produced in human cells transformed with adenovirus type 5 (Ad 5) E1 proteins, such as 293, 911 and PERC6 cells, indicates that the E1 protein enables this DNA virus to replicate to high titres in the presence of the apoptosis-inducing protein apoptin.

These results indicate that it is also possible to generate other recombinant DNA-virus vectors expressing apoptin in cell lines transformed by the adenovirus 5 E1 protein. For instance, the recombinant parvovirus vectors based on the H-1 or MVM parvoviruses can be propagated in 293T cells, which are transformed by Ad5 E1 protein (Dinsart et al., 1996).

The H-1 and MVM parvoviruses specifically induce cell death in transformed cells, but not in all (Lopez-Guerrero, 1997). Parvovirus vectors expressing apoptin will be more potent in inducing tumor-specific apoptosis than parvovirus as such, due to the additional tumor-specific induction of apoptosis by apoptin (Dinsart et al., 1996, Danen-Van Oorschot, 1997).

A protocol of the production of recombinant-apoptin virus vectors based on Ad5 E1 protein transformed cells, also holds true for RNA-virus species, such as retroviruses.

Induction of Apoptosis in Human Transformed and/or Malignant Cell Lines

Figure 4:
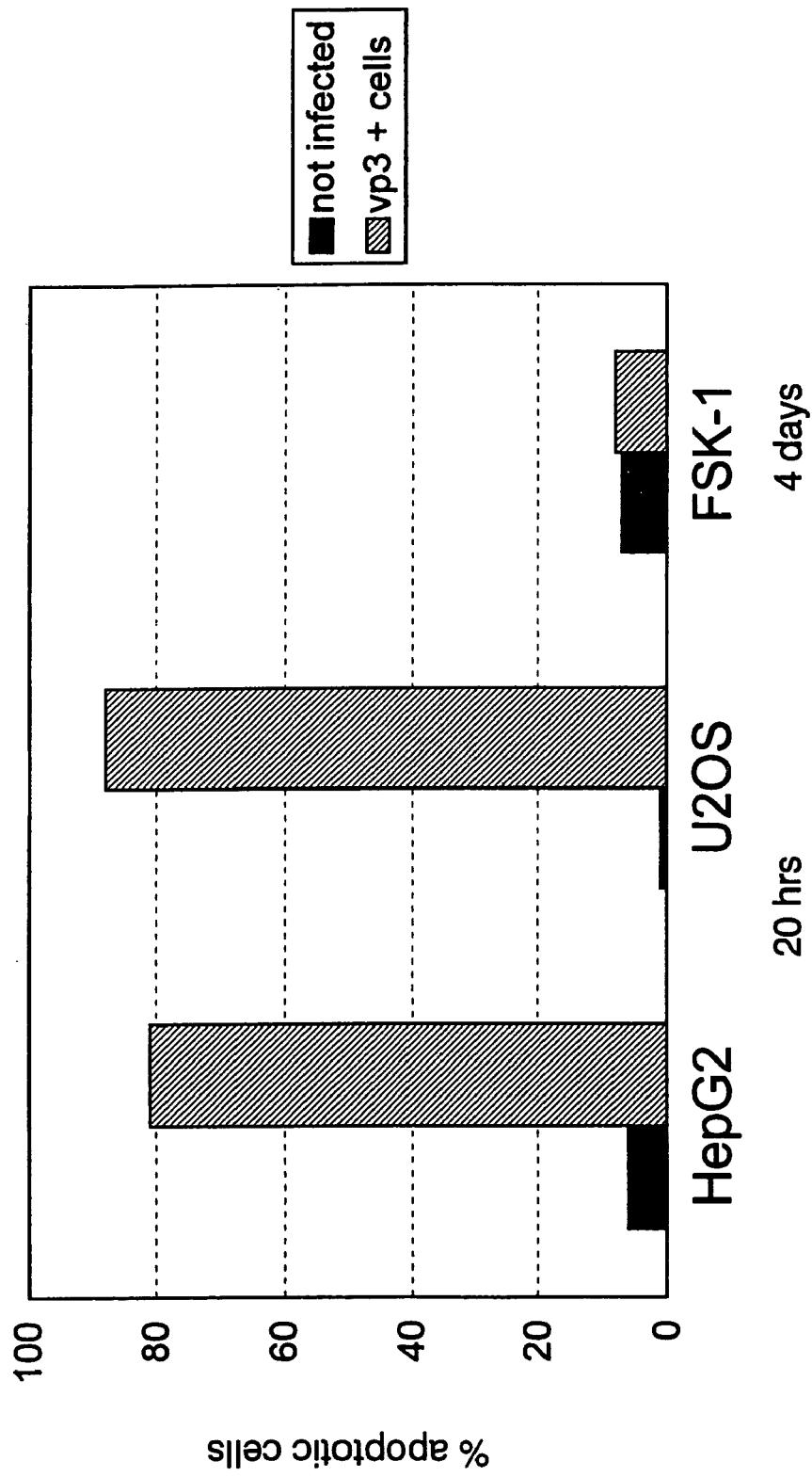
FIG. 4 shows the apoptin (called VP3)-induced activity of human tumorigenic hepatoma HepG2 cells, osteosarcoma U2OS cells and normal non-transformed diploid FSK-1 keratinocytes infected with the recombinant-apoptin replication-defective adenovirus Ad-VP3. The cells were analyzed by indirect immunofluorescence using the monoclonal antibody 85.1 and stained with DAPI. The HepG2 and U2OS cells were fixed 1 day after transfection and the FSK-1 cells were harvested and fixed 4 days after transfection. The percentage of apoptin-positive cells that stained abnormally with DAPI is given as a measure for apoptin-induced apoptosis (black boxes). As a control, the percentage of non-infected cells that have become DAPI-abnormally stained is given (open boxes).

We have examined whether infection of human tumor cells with rAd-VP3 will result in apoptin-induced apoptosis. To that end, human hepatoma HepG2, osteosarcoma U2OS cells, SCC-15 cells, derived from a squamous cell carcinoma, and cells from the spontaneously transformed keratinocyte cell line HaCaT were infected with rAd-VP3. One day after transfection, the cells were fixed and by means of immunofluorescence and DAPI staining the cells were examined for apoptin synthesis, and whether they have underwent apoptosis. Already, 1 day after infection almost all analysed apoptin-positive human tumor cells were apoptotic. In non-infected cultures, only a few percent of the human tumor cells were apoptotic. The results for HepG2 and U2OS cells are shown in FIG. 4.

These results indicate that rAd-VP3-expressed apoptin can induce apoptosis in different mammalian tumorigenic and/or transformed cell lines.

Expression of Apoptin in Normal Cells Infected with rAd-VP3

To analyse the effect of apoptin expressed by rAd-VP3 in infected normal non-transformed cells, FSK-1 cells were infected with rAd-VP3. Four days after transfection, the cells were analysed by indirect immunofluorescence using the monoclonal antibody 85.1 and DAPI-staining. At most 8% of the apoptin-positive cells showed a DAPI-abnormal staining, indicating that they might have underwent (apoptin)-induced apoptosis. However, 7% of the cells that were not infected also had a aberrant DAPI-stained DNA pattern. The results are shown in FIG. 4.

Given the hepatotropic nature of human Ad5 after systemic delivery, it is also of importance to investigate the effect of apoptin in normal diploid hepatocytes. To that end, isolated rat hepatocytes were cultured in Williams E medium (Gibco/Life Technologies, Grand Island, N.Y., USA) supplemented with insulin (2 mU/ml) and dexamethasone (1 nX). The cells were grown on collagen-coated culture slides (Micronic).

The primary rat hepatocytes were infected by the adenoviral vector Ad-VP3 expressing apoptin, a control adenovrius expressing LacZ, or mock-infected. After two days, the cells were fixed and by means of immunofluorescence and DAPI-staining the percentage of apoptotic cells was examined. No difference was observed in the percentage of dead cells either expressing apoptin, lacZ or mock-infected cells. These observations indicate that (rat) hepatocytes do not undergo apoptin-induced apoptosis, also when apoptin is synthesized by means of an adenovirus vector.

These results indicate that rAd-VP3-directed expression of apoptin does not result in apoptin-induced apoptosis in normal non-transformed human cells, in contrast to transformed/tumorigenic human cells.

Increasement of the Synthesis of Apoptin

To examine the effect of the direct sequences in front of the apoptin ATG-initiation codon, we have made two pCR-3.1-apoptin constructs. pCR-VP3ori contains the original direct upstream sequences (5'-TTTCAA-3') SEQ ID NO: 3 of the ATG-codon, whereas the other one, pCR-Vp3mu contains the direct upstream sequence (5'-GCCAAC-3') SEQ ID NO:4. By means of an in-vitro transcription/translation wheat-germ assay, it was determined that the apoptin expression of the pCR-VP3mu was at least 5 times more than observed for pCR-VP3ori. These data indicate that the nature of the direct upstream sequences of the apoptin-ATG influences the synthesis of apoptin. Construction of (viral) vectors with the direct upstream sequence (5'-GCCAAC-3') SEQ ID NO:4 in front of the ATG-codon of apoptin, will result in a higher apoptin production and indirectly in an increased apoptin-induced apoptosis.

Important to mention is also that the amino-acid sequence of apoptin is not altered as predicted to be necessary for increased translation efficiencies according the "Kozak rule" (Caventer and Stuart, 1991). According to this rule, we should have changed the nucleotide at position +4 from an A into a G, resulting into a different second amino acid of apoptin which would have changed its activity.

Identification of an Essential Apoptin Fragment Containing Apoptotic Activity

To examine whether a part of the apoptin protein is essential for its apoptotic activity, a plasmid was constructed encoding chimeric proteins, consisting of the Green-fluorescence protein (GFP; Rizzuto, 1995) and the N-terminal 71 amino acids of apoptin (N-apoptin) or its C-terminal 50 amino acids (C-apoptin). Human transformed cells, such as Saos-2 cells (Zhuang, 1995) were transiently transfected with the plasmids expressing chimeric GFP/N-apoptin or GFP/C-apoptin. Only, the Saos-2 cells expressing the GFP/C-apoptin underwent apoptin-specific apoptosis. This coincides with the fact that C-apoptin (linked to GFP) can enter the nucleus.

These results indicate that a part of apoptin can also be sufficient to induce apoptosis in (human) tumorigenic/transformed cells. Therefore, one can also develop an effective (gene) therapy based on (virus) vectors expressing only that part of apoptin. Furthermore, these data indicate that a part of apoptin contains its apoptotic acitivity when covalently linked to a foreign protein.

Co-expression of VP2 and Apoptin in Human Tumor Cells Synergistically Increases the Induction of Apoptosis To examine the effect of co-expression of VP2 and apoptin on the induction of apoptosis, Saos-2 cells were (co)-transfected with pCMV-fs, expressing apoptin and/or pCMV-VP2mu, expressing VP2. The cells were fixed with aceton at various time intervals after transfection. By indirect immunofluorescence, the VP2-positive cells were determined with monoclonal antibody CVI-CAV-111.1 (Noteborn and Koch, 1996) and the apoptin-positive cells with monoclonal antibody CVI-CAV-85.1. At day 3 after transfection, only 3% of the VP2-expressing cells underwent apoptosis, and only about 10% of the apoptin-expressing cells. In contrast, about 40% of the Saos-2 cells expressing both VP2 and apoptin were already apoptotic Also 4 days after transfection, the percentage of VP2/apoptin-positive cells that underwent apoptosis was significantly higher than in cells expressing apoptin or VP2 alone.

Figure 5:
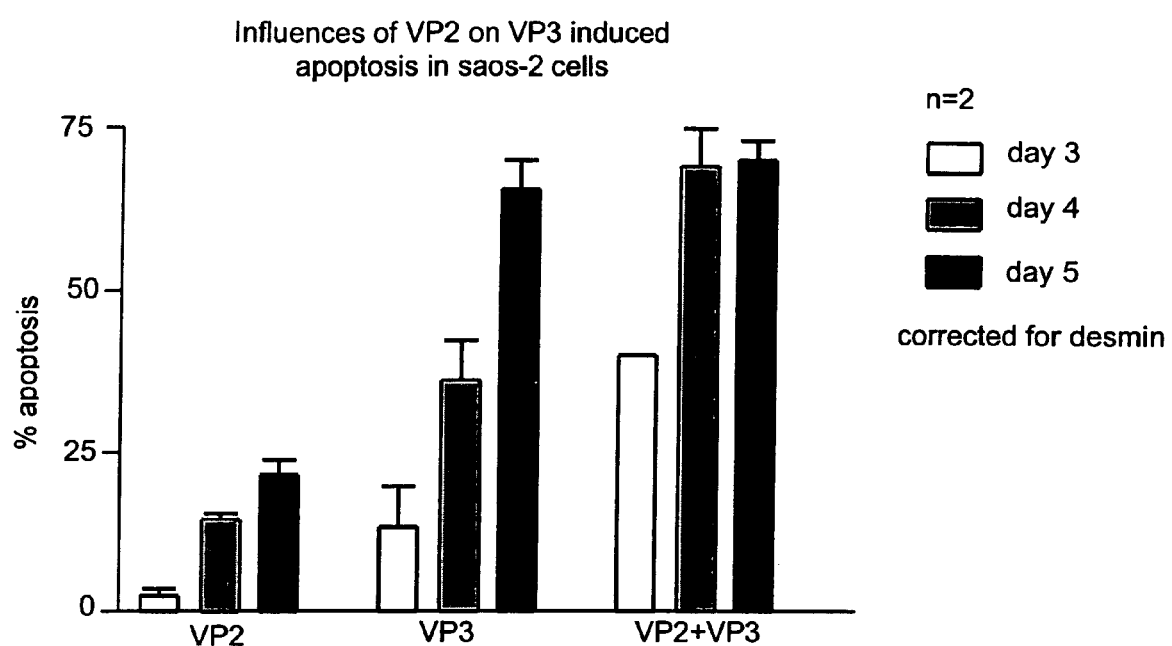
FIG. 5 shows the apoptin- and/or VP2-induced apoptosis activity in Saos-2 cells transfected with 2.5 µg of pCMV-fs DNA expressing apoptin (formerly called pCMV-VP3; apoptin is named VP3) and 2.5 µg of pCMV-neoBam DNA (Danen-Van Oorschot, 1997); or with 2.5 µg pCMV-VP2 DNA expressing he CAV protein 2 (VP2), and 2.5 µg of 2.5 µg of pCMV-neoBam DNA; or with 2.5 µg pCMV-fs and 2.5 µg pCMV-VP2 resulting in the expression of both apoptin (VP3) and VP2. The cells were fixed 3, 4 and 5 days after transfection and analyzed by indirect immunofluorescence using the apoptin-specific monoclonal antibody CVI-CAV-85.1 or with monoclonal antibody CVI-CAV-111.1 (Noteborn and Koch, 1996). The percentage of cells that stained abnormally with DAPI is given as a relative measure for apoptosis.

These results show that VP2 enhances the apoptin-induced apoptosis and are shown in FIG. 5.

Construction and Production of rAD-VP2

Figure 6:
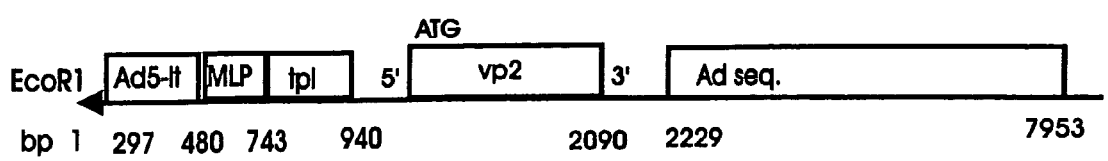
FIG. 6 shows the diagrammatic representation of the essential parts of the recombinant adenovirus adaptor vectors pMab-VP2.
Figure 6:
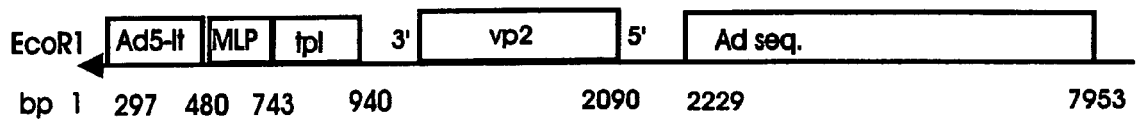

To construct a recombinant Adenovirus expressing the viral protein 2 (VP2) of chicken anemia virus, the adaptor plasmid pMAb-VP2 was made. A 1.1-kb BamHI fragment was isolated from the plasmid pCMV-VP2mu containing all VP2 coding sequences, but with 2 point mutations within the apoptin-coding region (see Experimental section) and ligated into the BamH1-linearized and calf intestine alkaline phosphatase-treated adaptor vector pMAb. The final construct pMab-VP2 was characterized by restriction-enzyme and sequence analysis and shown in FIG. 6.

By co-transfection of 911 cells with pMab-VP2 DNA and pJM17 DNA, rAD-VP2 was made. The co-transfection and all other required steps needed for characterization, purification and production of rAd-VP2, were carried out as described for rAd-VP3 and rAd-con. By indirect immunofluorescence using monoclonal antibody CVI-CAV-111.1, it was shown that 911 and PER.C6 cells infected with rAd-VP2, indeed could express VP2 protein.

Construction of a Retrovirus Vector Expressing Apoptin

Figure 7:
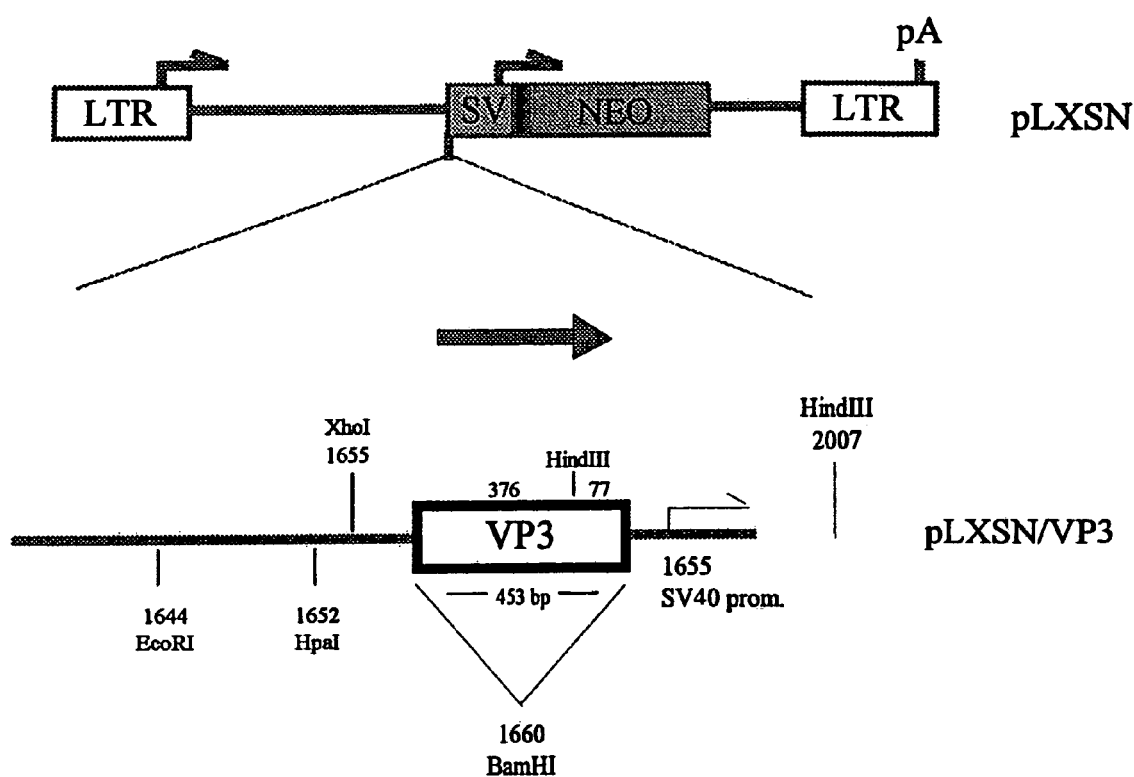
FIG. 7 shows the diagrammatic representation of the essential parts of the recombinant retrovirus transfer vector pLS-VP3-N.

To generate plasmid pL-VP3-SN (see FIG. 7), a BamHI fragment carrying the apoptin-coding sequences were inserted in the unique BamHI site of pLXSN. With restriction-enzyme analysis the proper orientation of the insert was confirmed. To test the integrity of the insert the plasmid pL-VP3-SN was transfected with the calcium phosphate co-precipitation technique in COS-7 and HepG2 cells. Four days after transfection, the cells were fixed and analyzed with monoclonal antibody 85.1 for the expression of the apoptin protein. In appoximately 1–2% of the cells, apoptin expression could be detected. The majority of the cells underwent apoptosis, as determined by DAPI staining. These data show that the proviral LTR promoter is capable of driving the expression of the apoptin protein, that its gene is intact in the DNA construct and that in transfected HepG2 and COS-7 cells the expression of apoptin induces apoptosis.

To generate viruses the plasmid pL-VP3-SN was transfected into Psi-2 cells and into PA 317 cells with the calcium phosphate co-precipitation technique. Fourty-eight hours after transfection, the supernatant of the cells wass harvested and dilutions were used to infect HepG2 cells (the PA317 supernatant) and NIH3T3 cells (the Psi-2 supernatant) in the presence of 4 ug/ml polybrene. Four days after infection, the cells were fixed and analysed for apoptin expression by staining with the monoclonal antibody 85.1. Approximately 1% of the cells were found to express apoptin. The majority of the apoptin-positive HepG2 cells were apoptotic. These data demonstrate that the cells had been transduced with the L-apoptin-SN retroviruses. In addition, it demonstrates that a single copy of the provirus is sufficient to express sufficient amounts of the apoptin protein to be detected by immunofluorescence, and this amount is sufficient to induce apoptosis in a human tumor cell line, namely the hepatoma cell line HepG2.

Taken together, these data demonstrate that retrovirus vectors carrying the apoptin gene can be generated and can be used to induce apoptosis in human tumor cells. It formally proves that neither the apoptin gene nor its expression interfere with essential steps in the retrovirus life cycle. It also demonstrates that apoptin-containing retroviruses can be produced batch-wise in quantities sufficient to be used to transduce human tumor cells in tissue culture.

These results further imply that apoptin expression, and consequently apoptin-induced apoptosis in (human) tumor cells, will also be possible by means of (retro)-virus-derived vector systems, such as plasmoviruses (Noguiez-Hellin, 1996). The critical step for such a recombinant-apoptin plasmovirus system is whether the retrovirus replication is not blocked by the expression of apoptin. We have provided evidence that this indeed is not the case, for the above-described recombinant-apoptin retrovirus implying successful production of recombinant-apoptin plasmovirus.

Diagnostic Assay for Cancer Cells Based on rAD-VP3

The cellular location of apoptin is different in tumorigenic/transformed human cells in comparison to normal non-transformed cells. Furthermore, another marker is the specific ability of apoptin to induce apoptosis in tumorigenic/transformed cells and not in normal cells.

By infecting cells with rAd-VP3 and analyzing the apoptin location and/or induction of apoptosis within these cells, one is able to prove whether a cell is malignant or not. Primary cells are isolated from (suspicious) tissue and cultured in the required medium. The cells are infected with rAd-VP3 and in parallel with rAd-con, and subsequently analyzed. For instance, by using an immunofluoreacence assay based on monoclonal antibodies specific for apoptin, 85.1. The cells will be checked for having apoptin in the cytoplasm (normal cells) or in the nucleus (transformed cells). In addition or instead of, the percentage of apoptotic cells will be estimated. If the percentage of apoptotic cells is significantly higher for rAd-Vp3- than for rAd-con-infected cells, these cells have become malignant.

Toxicity experiments of recombinant-apoptin adenovirus in healthy rats.

Under tissue culture conditions, apoptin expressed by the recombinant adenovirus rAd-VP3 in normal cells, e.g. derived from human or rodent origin, does not induce apoptosis. In the experiment described below, we have examined whether expression of apoptin by means of the recombinant adenovirus vector rAd-Vp3 in healthy rats does not result in acute toxicity.

The used rAd-VP3 vector and a control rAd vector were both grown on PER.c6 cells and by PCR analysis proven to be negative for replication-competent adenovirus (RCA-free). The rAd's were purified by means of CsCl-gradient centrifugation.

Male Wag/Rij rats (Harlan, The Netherlands) with a body weight of about 200 gram were injected with recombinant adenovirus expressing apoptin (rAd-VP3; $2.5 \times 10^9$ plaque forming units, pfu), with control recombinant adenovirus expressing the geneproduct luciferase (rAd-luc; $2.5 \times 10^9$). Both adenovirus vectors were resuspended in phosphate-buffered saline, containing 0.1% bovine serum albumin, and 10% glycerol (PBS+). This solution without adenovirus vector was also injected in rats and serves as additional negative control. Two rats were injected intravenously, intraperitoneally or subcutaneously, either with rAd-VP3, rAd-luc or PBS+suspension.

Macroscopic pathological analysis of Ad-VP3-treated rats.

The first method to examine a possible toxic effect of Ad-VP3-expressed apbptin was to determine the general health condition and in particular the body weight of the treated rats, which was done every day following the injections. All rats were in good health condition during the experiment. The body weight was not significantly different in the various groups. After 1 week, all examined rats, including those injected with rAd-VP3, had gained body weight indicating that none of the animals was suffering an acute toxicity due to one of the treatments with rAd-VP3. To further establish the absence of acute toxicity the following determinations were carried out. Two hours before sacrifice, all rats were injected with BrdU. After sacrifice, several tissues (liver, kidney, intestines, heart, lung, spleen, gonads and penis) were pathologically examined directly and/or collected for further histopathologic analysis (see below).

Macroscopic analysis showed that none of the Ad-VP3-treated rats had organs with significant pathological effects.

Determination of Ad-VP3 DNA in the liver.

The main target of intravenously injected (recombinant) adenovirus (vector) is the liver and to some extent the spleen. Therefore, any toxic effects of apoptin will be observed in the liver.

A panel of experiments were carried out to examine the presence of Ad-VP3 DNA, apoptin expression by Ad-VP3 and a possible cyto-pathological effect in the liver. First, we have examined by Southern blot analysis whether isolated DNA from livers of Ad-VP3-treated rats contained the apoptin DNA at the day of sacrifice, which means 8 days after injection. As negative controls, the DNA from the livers of Ad-luc-treated rats were examined in parallel. Before, loading the isolated DNA on a agarose gel the DNA was digested with BamHI, which results in a apoptin DNA fragment of about 0.5 kbp. The Southern blot was hybridized with a $^{32}$P-labeled apoptin-DNA probe.

The apoptin BamHI-DNA fragment was clearly visible on the Southern blot in case of DNA derived from the Ad-VP3-treated animals, and as expected absent in the lanes containing the DNA isolated from livers of rats treated with the control rAd-luc. To examine the amount of Ad-VP3 copies in the liver, various amounts of apoptin DNA were loaded on parallel on the Southern-blot and hybridized with the labeled apoptin-DNA probe. Even eight days after intravenously infection, 0.25 Ad-VP3 copies per cell could be determined, which indicates a very significant transduction of Ad-VP3 in the liver.

Expression of apoptin and its toxic effect in liver cells.

By means of immunostaining of paraffin sections of livers treated with Ad-Vp3 or control livers using the apoptin-specific monoclonal antibodies CVI-CAV-85.1 or CVI-CAV-111.3., we have shown that about 20–30% of the liver cells of the Ad-VP3-treated animals had expressed apoptin. The liver sections of the control rats were negative for apoptin.

To examine the possible cyto-toxic effects on Ad-VP3-expressed apoptin on liver cells, two different methods were carried out. First, the liver sections of all Ad-VP3-treated rats and those of both types of control animals were stained with haematoxyline-eosine (HE). For all examined liver sections no morphological pathological changes could be observed, indicating that apoptin expression is not toxic for rat liver cells.

Damaging effects can be seen by means of BrdU-labeling that detect newly divided liver cells. In case of Ad-VP3-containing liver the amount of BrdU-labeled liver cells was to a similar extent (about 2%) as control Ad-luc-treated rat livers. Therefore, apoptin expression, as such, has no significant toxic effect in vivo.

Apoptin has no acute toxic effect in an in-vivo model.

Both macroscopic, as well as, histological analysis in combination with biochemical and immunological data revealed that expression of apoptin has no (acute) toxic effect in an in-vivo model.

These results indicate that a therapy based on expression of apoptin by use of a gene-delivery vehicle or by other methods will have limited negative side effects.

Anti-tumor studies in a human hepatoma model.

Ad-VP3-regulated expression of apoptin results in the induction of apoptosis in human transformed cells under tissue-culture conditions. For instance, Ad-VP3-driven apoptin expression results in induction of apoptosis in the human hepatoma-derived cells HepG2. Thusfar, no in-vivo anti-tumor activity of apoptin (e.g. expressed by Ad-VP3) was examined.

Therefore, we have determined whether Ad-VP3-regulated apoptin expression will result in an anti-tumor activity in an in-vivo model. To that end, male nude Balb/C/nu/nu mice were injected subcutaneously with $1\times10^6$ human HepG2 cells per side. At least at two or three locations per mouse human hepatoma cells were injected. Three weeks after injection clear hepatoma tumors had developed, were subcutaneously visible and had a mean size of at least 5×5 mm.

The rAd-VP3 and control rAd-con1 vectors, suspended in phosphate-buffered saline, 5% sucrose and 0.1% bovine serum albumin, were intra-tumorally injected.

The used rAd-VP3 vector expressing apoptin and the control vector rAd-con1 containing the apoptin gene in the 3'–5' (reverse or anti-sense) orientation opposite to the Ad MLP promoter were both grown on PER.c6 cells. Both batches of recombinant adenoviruses were proven to be RCA-free by means of PCR analysis. The rAd's were purified by use of CsCl-gradient centrifugation.

Per tumor $7\times10^9$ pfu rAd particles in 40 micro-liter suspension were injected. Per type rAd vector 6 mice with 2 to 3 HepG2 tumors were treated. As additional control, a group of 4 nude mice containing HepG2 tumors were intra-tumorally injected with phosphate-buffered saline containing 5% sucrose and 0.1% bovine serum albumin (PBS+-group).

Apoptin has an anti-tumor effect in an in-vivo model.

To examine the possible anti-tumor effect of Ad-VP3 expressed apoptin in the human HepG2 tumors, the size of the subcutaneous tumors were measured during the experiment which continued till 7 days after injection of the rAd-VP3 and control suspensions.

Both the PBS+ group and the group treated with control rAdcon1 showed a mean progressive increase of HepG2 tumor size. In contrast, to the group that was intra-tumorally treated with rAdVP3, which showed a reduced tumor size. At seven days after injection, the nude mice were sacrificed. The tumors were isolated and macroscopically examined. It is clear that the hepatoma tumors treated with the control rAd-con1 vector or PBS+showed to be heavily vascularized HepG2-tumor tissue and had been become bigger after treatment. A complete different pattern was observed with the rAd-VP3-treated HepG2 tumors. The residual tumor mass had a pale appearance, due to a reduced tumor vascularization. The tumors had become reduced in size after treatment with rAd-VP3. The tumors contained also white bubble-like structures, which is indicative for dead cells.

Besides the apoptin-induced tumor regression, no negative effect of apoptin-expression on the organs (in particular liver and spleen were examined) could be observed.

Apoptin has anti-tumor activity in an in-vivo system.

In conclusion, tumors treated with rAd-VP3 showed a reduced tumor size, whereas the controls did not. This implies that expression of apoptin has an anti-tumor activity in an in-vivo model.

The fact that Ad-VP3-expressed apoptin can induce tumor regression in a fast-growing tumor as HepG2 proves the strong anti-tumor potential of apoptin. The fact that apoptin reduces tumor growth in nude mice shows that expression of apoptin itself 'kills' the tumor cells without an additional immune response.

The described toxicity and anti-tumor studies reveal that an anti-tumor therapy based on expression of apoptin is safe and feasible.

REFERENCES

1. Aden, D. P., Fogel, A., Plotkin, S., Damjanov, I., and Knowles, B. B, (1979). Controlled synthesis of HBsAg in a differentiated human liver carcinoma-derived cell line. Nature 282, 615–616.
2. Arends, M. J., and Wyllie, A. H. 1991. Apoptosis; mechanisms and roles in pathology. International review of experimental pathology 32, 223–254.

3. Bellamy, C. O. C., Malcomson, R. D. G., Harrison, D. J., and Wyllie, A. H. 1995. Cell death and disease: The biology and regulation of apoptosis. Seminars on Cancer Biology 6, 3–12.
4. Boukamp, P., Petrussevska, R. T., Breitkreutz, Hornung, J., Markham, A., and Fusenig, R. 1988. Normal keratinazation in a spontaneously immortalized aneuploid human keratinocyte cell line. Journal of Cell Biology 106, 761–771.
5. Cavener, D. R. and Stuart, C. R. (1991). Eukaryotic start and stop translation sites. Nucleic Acids Research 19, 3185–3192.
6. Danen-Van Oorschot A. A. A. M., Fischer D., Grimbergen J. M., Klein B., Zhuang S.-M., Falkenburg J. H. F., Backendorf C., Quax P. H. A., Van der Eb A. J., and Noteborn M. H. M. (1997). Apoptin induces apoptosis in human transformed and malignant cells but not in normal cells. Proceedings National Academy Sciences, USA: In press.
7. Diller, L. et al., (1990). p53 functions as a cell cycle control protein in osteosarcomas. Molecular Cellular Biology 10, 5772–5781.
8. Dinsart, C., Cornelis, J., Rommelaere, J. (1996). Recombinant autonomous parvoviruses: New tools for the gene therapy of cancer? Chimica Oggi/chemistry today. September 1996, 32–38.
9. Earnshaw, W. C., 1995. Nuclear changes in apoptosis. Current opinion in Cell Biology 7, 337–343.
10. Fallaux, F. (1996). Gene therapy for hemophilia A: Towards the use of adenovirai vectors? PhD Thesis, Leiden University, The Netherlands.
11. Fallaux F., Kranenburg, Cramer S. J., Houweling, A., Van Ormondt, H., Hoeben, R. C., and Van der Eb, A. J. (1996) Human Gene Therapy 7, 215–222.
12. Fischer, D. F., Gibbs, S., Van De Putte, P., and Backendorf, C. (1996). Molecular Cellular Biology 16, 5365–5374.
13. Graham, F. L. and Prevec, L. (1991). Manipulation of adenovirus vectors. In: Methods in Molecular Biology. Volume 7: Gene Transfer and Expression Protols. E. J. Murray, ed. (The Humana Press, Clifton, N.J.) pp 109–128.
14. Graham, F. L. and Van der Eb, A. J. (1973). A new technique for the assay of infectivity of human adenovirus 5 DNA. Virology 52, 456–467.
15. Hockenberry, D. M. (1994). Bcl-2 in cancer, development and apoptosis. Journal of Cell Science, Supplement 18, 51–55.
16. Hooper, M. L. (1994). The role of the p53 and Rb-1 gene in cancer, development and apoptosis. Journal of Cell Science, Supplement 18, 13–17.
17. Horwitz, M. S. (1990). Adenoviridae and their replication. pp 1679–1740. In B. N. Fields and D. M. Knipe (Eds): Virology, Raven Press, Ltd, New York.
18. Kerr, J. F. R., Winterford, C. M., and Harmon, B. V. (1994). Apoptosis: Its significance in cancer and cancer therapy. Cancer 73, 2013–2026.
19. Levrero, M., Barban, V., Manteca, S., Ballay, A., Balsano, C., Avantaggiati, M. L., Natoli, G., Skellekens, H., Tiollais, P., and Perricaudet, M. (1991). Defective and non-defective adenovirus vectors for expressing foreign genes in vitro and in vivo. Gene 101, 195–202.
20. Lopez-Guerro, J. A., Rayet, B., Tuynder, M., Rommelaere, J., and Dinsart, C. (1997). Constitutive activation of U937 promonocytic cell clones selected for their resistance to parvovirus H-1 infection. Blood 89, 1642–1653.
21. Maniatis, T., Fritsch, E. F., and Sambrook, J. (1982). Molecular Cloning: A Laboratory Manual. CSHL Press, New York, USA.
22. Mann, R., Mulligan, R. C., and Baltimore, D. (1983). Cell 33, 153–159.
23. McGrory, W. J., Bautista, D. S., and Graham, F. L. (1988). A simple technique for the rescue of early region I mutations into infectious human adenovirus type 5. Virology 163, 614–617.
24. Miller, A. D. (1990a). Progress towards human gene therapy. Blood 76, 271–278.
25. Miller, A. D. (1990b). Retrovirus packaging cells. Human Gene Therapy, 1, 5–14.
26. Noguiez-Hellin, P., Robert-LeMeur, M., Salzmann, J. L., and Klatzmann, D. (1996). Plasmoviruses: nonviral/viral vectors for gene therapy. Proc. Natl. Acad. Sci. USA 93, 4175–4180.
27. Noteborn, M. H. M. (1996). PCT application WO 96/41191 Apoptin induces apoptosis in human transformed and malignant cells but not in normal cells as essential characteristic for the development of a antitumor therapy.
28. Noteborn, M. H. M. and De Boer, G. F. (1995). Patent U.S. Pat. No. 5,491,073. Noteborn, M. H. M. and Koch, G. (1996). PCT application WO 96/40931 chicken anemia virus vaccines containing neutralizing conformational epitope.
29. Noteborn, M. H. M., De Boer, G. F., Kant, A., Koch, G., Bos, J. L., Zantema, A., and Van der Eb, A. J. (1990). Expression of avian leukemia virus env-gpB5 in *Spodoptera frugiperda* cells by use of a baculovirus expression vector. Journal of general Virology 71, 2641–2648.
30. Noteborn, M. H. M., De Boer, G. F., Van Roozelaar, D., Karreman, C., Kranenburg, O., Vos, J., Jeurissen, S., Zantema, A., Hoeben, R., Koch, G., Van Ormondt, H., and Van der Eb, A. J. (1991). Characterization of cloned chicken anemia virus DNA that contains all elements for the infectious replication cycle. Journal of Virology 65, 3131–3139.
31. Noteborn M. H. M. and Koch G. (1995). Chicken anaemia virus infection: molecular basis of pathogenicity. Avian Pathology 24: 11–31.
32. Noteborn M. H. M., Koch G., Verschueren C. A. J., De Gauw H. W. F. M., Veldkamp S., Van der Eb A. J. (1994). A single anaemia virus protein, apoptin, causes cytopathogenic effect by inducing apoptosis. In: Proceedings of the international symposium on infectious bursal disease and chicken infectious anaemia (Kaleta EF, ed) pp 376–381, Rauischholzhausen, Germany.
33. Noteborn M. H. M., Todd D., Verschueren C. A. J., De Gauw H. W. F. M., Curran W. L., Veldkamp S., Douglas A. J., McNulty M. S., Van der Eb A. J., Koch G. (1994). A single chicken anemia virus protein induces apoptosis. J. Virology 68: 346–351.
34. Rheinwald, J. and Beckett, M. A. (1980). Defective terminal differentiation in cultures as a consistent and selectable character of malignant human keratinocytes. Cell 22, 629–632.
35. Rheinwald, J. G., and Green, H. (1975). Serial cultivation of strains of human epidermal keratinocytes: The formation of keratinizing colonies from single cells. Cell 6, 331–343.
36. Rizzuto, R. (1995). Chimeric green fluorescent protein as a tool for visualizing subcellular organels in living cells. Curr. Biol. 5, 635–642.

37. Sachs, L. and Lotern, J. (1993). Control of programmed cell death in normal and leukemia cells: New implications for therapy. Blood 82, 15–21.
38. Steller, H. (1995). Mechanisms and genes of cellular suicide. Science 267, 1445–1449.
39. Stratford-Perricaudet, L. and Perricaudet, M. (1991). Gene transfer into animals: the promise of adenovirus, pp 51–61. In: O. Cohen-Adenauer and M. Boiron (eds): Human Gene Transfer, John Libbey Eurotext.
40. Thompson, C. B. (1995). Apoptosis in the pathogenesis and treatment of disease. Science 267, 1456–1462.
41. White, E. (1996). Life, death, and the pursuit of apoptosis. Genes and development 10, 1–15.
42. Wyllie, A. H. (1995). The genetic regulation of apoptosis. Current opinion in Genetics and Development 5, 97–104.

The invention claimed is:

1. A recombinant gene delivery vehicle comprising a nucleic acid molecule encoding a chicken anemia virus protein VP3.

2. A recombinant gene delivery vehicle comprising a nucleic acid molecule encoding a chicken anemia virus protein VP3, having a modified translation initiation site directly upstream of the ATG-initiation codon of said nucleic acid molecule, wherein said translation initiation site comprises the nucleic acid sequence GCCAAC.

3. A recombinant gene delivery vehicle comprising a nucleic acid molecule encoding a chicken anemia virus protein VP2.

4. A recombinant gene delivery vehicle comprising a nucleic acid molecule encoding a chicken anemia virus protein VP2, having a modified translation initiation site directly upstream of the ATG-initiation codon of said nucleic acid molecule, wherein said translation initiation site comprises the nucleic acid sequence GCCAAC.

5. The gene delivery vehicle according to claim 1 additionally comprising a nucleic acid molecule encoding chicken anemia virus protein VP2.

6. The gene delivery vehicle according to claim 2 additionally comprising a nucleic acid molecule encoding chicken anemia virus protein VP2, having a modified translation initiation site directly upstream the ATG-initiation codon of the nucleic acid molecule encoding chicken anemia virus protein VP2, wherein said translation initiation site comprises the nucleic acid sequence GCCAAC.

7. The gene delivery vehicle according to claim 1 which is a viral vector.

8. The gene delivery vehicle according to claim 7 wherein said viral vector is replication defective.

9. The gene delivery vehicle according to claim 8 wherein said viral vector is an adenoviral vector.

10. The gene delivery vehicle according to claim 8 wherein said viral vector is a retroviral vector.

11. The gene delivery vehicle according to claim 5 which additionally comprises at least one target molecule.

12. The gene delivery vehicle according to claim 11 wherein the target molecule is reactive with a tumor cell surface receptor.

13. A host cell comprising the gene delivery vehicle according to claim 12.

14. The host cell according to claim 13 which is a helper or packaging cell.

15. The host cell according to claim 13 which is selected from the group of HEK 293, HER 911, PER-C6, Psi-2, and PA-317 cells.

16. A method for inducing apoptosis in a mammalian tumor by directly administering to a tumor of a mammal the gene delivery vehicle of claim 1, wherein said nucleic acid molecule encoding the chicken anemia virus protein VP3 is operatively linked to a promoter.

17. A method for inducing apoptosis in a mammalian tumor by directly administrating to a tumor of a mammal the gene delivery vehicle of claim 5, wherein said nucleic acid molecule encoding the chicken anemia virus protein VP3 or VP2 is operatively linked to a promoter.

* * * * *

UNITED STATES PATENT AND TRADEMARK OFFICE
CERTIFICATE OF CORRECTION

PATENT NO. : 7,253,150 B1  Page 1 of 1
APPLICATION NO. : 09/403213
DATED : August 7, 2007
INVENTOR(S) : Matheus Hubertus Maria Noteborn and Alexandra Maria Pietersen It is certified that error appears in the above-identified patent and that said Letters Patent is hereby corrected as shown below:

On the title page:
In ITEM (56) References Cited
U.S. PATENT DOCUMENTS,
Page 1, 1st column, 5th entry,      change "5,952,002 A * 9/1999 Noteborn et al." to --5,952,002 A * 9/1999 Noteborn et al.--

In the specification:
| | | |
|---|---|---|
| COLUMN 6, | LINE 57, | change "by5 performing" to --by 5 performing-- |
| COLUMN 13, | LINE 13, | change "wass harvested" to --was harvested-- |
| COLUMN 13, | LINE 60, | change "immunofluoreacence" to --immunofluorescence-- |
| COLUMN 14, | LINE 32, | change "apbptin was" to --apoptin was-- |
| COLUMN 19, | LINE 1, | change "Lotern, J." to --Lotem, J.-- |

Signed and Sealed this

Thirtieth Day of September, 2008

JON W. DUDAS
*Director of the United States Patent and Trademark Office*

SEQUENCE LISTING

<160> NUMBER OF SEQ ID NOS: 6

<210> SEQ ID NO 1
<211> LENGTH: 19
<212> TYPE: DNA
<213> ORGANISM: Artificial Sequence
<220> FEATURE:
<223> OTHER INFORMATION: Description of Artificial Sequence: primer derived from Ad5 ITR region

<400> SEQUENCE: 1
gggtggagtt tgtgacgtg                                                  19

<210> SEQ ID NO 2
<211> LENGTH: 20
<212> TYPE: DNA
<213> ORGANISM: Artificial Sequence
<220> FEATURE:
<223> OTHER INFORMATION: Description of Artificial Sequence: primer derived from the E1A encoding region

<400> SEQUENCE: 2
tcgtgaaggg taggtggttc                                                 20

<210> SEQ ID NO 3
<211> LENGTH: 6
<212> TYPE: DNA
<213> ORGANISM: Artificial Sequence
<220> FEATURE:
<223> OTHER INFORMATION: Description of Artificial Sequence: upstream primer

<400> SEQUENCE: 3 tttcaa                                                                 6

<210> SEQ ID NO 4
<211> LENGTH: 6
<212> TYPE: DNA
<213> ORGANISM: Artificial Sequence
<220> FEATURE:
<223> OTHER INFORMATION: Description of Artificial Sequence: upstream primer

<400> SEQUENCE: 4 gccaac                                                                 6

<210> SEQ ID NO 5
<211> LENGTH: 19
<212> TYPE: DNA
<213> ORGANISM: Artificial Sequence
<220> FEATURE:
<223> OTHER INFORMATION: Description of Artificial Sequence: BamH1-ClaI linker forward

<400> SEQUENCE: 5

```
gatcccgcac gcgtgcgat                                              19
```

<210> SEQ ID NO 6
<211> LENGTH: 17
<212> TYPE: DNA
<213> ORGANISM: Artificial Sequence
<220> FEATURE:
<223> OTHER INFORMATION: Description of Artificial Sequence: BamH1-ClaI
      linker reversed

<400> SEQUENCE: 6

```
cgatcgcacg cgtgcgg                                                17
```